(12) United States Patent
Mevorat Kaplan et al.

(10) Patent No.: US 11,324,772 B2
(45) Date of Patent: May 10, 2022

(54) PERIODONTAL GEL COMPOSITION AND METHOD OF USE

(71) Applicant: PRUDENTIX LTD., Lod (IL)

(72) Inventors: Keren Mevorat Kaplan, Ness Ziona (IL); Dadi Segal, Tel-Aviv (IL); Danny Rosenbaum, Kfar Saba (IL); Igal Liapis, Vaughan (CA); Igor Makarovsky, Holon (IL); Meir Stern, Rehovot (IL)

(73) Assignee: PRUDENTIX LTD., Lod (IL)

( * ) Notice: Subject to any disclaimer, the term of this patent is extended or adjusted under 35 U.S.C. 154(b) by 69 days.

(21) Appl. No.: 16/487,337

(22) PCT Filed: Feb. 27, 2018

(86) PCT No.: PCT/IL2018/050218
§ 371 (c)(1),
(2) Date: Aug. 20, 2019

(87) PCT Pub. No.: WO2018/158764
PCT Pub. Date: Sep. 7, 2018

(65) Prior Publication Data
US 2020/0054667 A1    Feb. 20, 2020

(30) Foreign Application Priority Data

Feb. 28, 2017 (IL) .......................................... 250853

(51) Int. Cl.
*A61K 31/728*   (2006.01)
*A61K 47/32*   (2006.01)
*A61K 9/00*   (2006.01)
*A61P 1/02*   (2006.01)
*A61K 9/06*   (2006.01)
*A61P 29/00*   (2006.01)
*A61K 31/444*   (2006.01)

(52) U.S. Cl.
CPC .......... *A61K 31/728* (2013.01); *A61K 9/0014* (2013.01); *A61K 9/06* (2013.01); *A61K 31/444* (2013.01); *A61K 47/32* (2013.01); *A61P 1/02* (2018.01); *A61P 29/00* (2018.01)

(58) Field of Classification Search
CPC ........ A61K 31/728; A61K 31/444; A61P 1/02
See application file for complete search history.

(56) References Cited

U.S. PATENT DOCUMENTS

| 4,906,670 A | 3/1990 | Higashi et al. |
| 6,136,297 A | 10/2000 | Sagel et al. |
| 2012/0277199 A1* | 11/2012 | Ye .......................... A61P 31/04 514/171 |
| 2015/0366975 A1 | 12/2015 | Jhan et al. |

FOREIGN PATENT DOCUMENTS

| CN | 105168238 A | 12/2015 |
| DE | 202016102375 U1 | 5/2016 |
| EP | 2520279 A1 | 11/2012 |
| WO | WO-2007/031520 A2 | 3/2007 |

OTHER PUBLICATIONS

Xu et al; "Preparation and in vitro characterization of thermosensitive and mucoadhesive hydrogels for nasal delivery of phenylephrine hydrochloride" European Journal of Pharmaceutics and Biopharmaceutics vol. 88, Issue 3, pp. 998-1004. (2014).
Extended European search report dated Nov. 26, 2020 (3 pages).
International Application No. PCT/IL2018/050218, International Search Report and Written Opinion, dated May 21, 2018.
Yadav et al., Advances in patents related to intrapocket technology for the management of periodontitis, Recent Pat. Drug. Deliv. Formul. 9:129-45 (2015).

* cited by examiner

*Primary Examiner* — Pancham Bakshi
(74) *Attorney, Agent, or Firm* — Marshall, Gerstein & Borun LLP

(57) ABSTRACT

The present invention relates to a periodontal gel composition, more particularly to a liquid composition having a low viscosity at ambient temperature, which upon warming to body temperature solidifies into a viscous gel and then releases a therapeutic agent, e.g., an antibacterial agent, in a sustained release manner; and to a method of use.

26 Claims, 1 Drawing Sheet

Fig. 2A              Fig. 2B

PERIODONTAL GEL COMPOSITION AND METHOD OF USE

CROSS REFERENCE TO RELATED APPLICATIONS

This application is the U.S. National Phase under 35 U.S.C. § 371 of International Application No. PCT/IL2018/050218 filed Feb. 27, 2018, designating the U.S. and published as WO 2018/158764 on Sep. 7, 2018, which claims the benefit of Israel Patent Application No. 250853, filed Feb. 28, 2017. Any and all applications for which a foreign or domestic priority claim is identified above and/or in the Application Data Sheet as filed with the present application are hereby incorporated by reference under 37 CFR 1.57.

TECHNICAL FIELD

The present invention relates to a periodontal gel composition, more particularly to a liquid composition having a low viscosity at ambient temperature, which upon warming to body temperature solidifies into a viscous gel and then releases a therapeutic agent, e.g., an antibacterial agent, in a sustained release manner; and to a method of use.

BACKGROUND ART

Periodontal diseases are common ailment which affect high proportion of the population especially at advanced age. Gingivitis, often caused by inadequate oral hygiene, is the mildest form of a periodontal disease that causes the gingiva (or gums) to become red, swollen, and bleed easily. While gingivitis can be reversible with professional treatment and good oral home care, untreated gingivitis can advance to periodontitis. With time, plaque can spread and grow below the gum line. Toxins produced by the bacteria in plaque irritate the gums, and stimulate a chronic inflammatory response following which the tissues and bone supporting the teeth are broken down and destroyed. Consequently, gums separate from the teeth, forming pockets (spaces between the teeth and gums) that become infected. As the disease progresses, those pockets deepen and more gum tissue and bone are destroyed. Often, this destructive process has very mild symptoms. Eventually, teeth may become loose and might have to be removed.

In contrast to the tooth's carries that might be rather effectively treated, periodontal diseases are more difficult to treat, inter alia, due to the markedly different environments of the oral and periodontal cavities. In particular, whereas the oral cavity is essentially an aerobic environment constantly perfused by saliva, the periodontal microenvironment is more anaerobic and perfused by a plasma filtrate known as the "crevicular fluid". The growth of microorganisms within the periodontal microenvironment may cause periodontal disease, and as the periodontal disease becomes more established, said microenvironment becomes more anaerobic and the flow of crevicular fluid increases. The increased outward flow of said fluid prevents therapeutic agents placed within the oral cavity from entering the periodontal pocket, and has the effect of diluting and removing therapeutic agents placed within the periodontal crevice. Thus, antimicrobial agents introduced to the oral cavity are generally ineffective.

Indeed, antibacterial agents such as chlorhexidine and quaternary ammonium salts, in the form of mouth rinses, have proved to be successful in preventing periodontal disease (Loe et al., 1970). Yet, when administered in the form of mouth rinses, these agents have little effect on the subgingival flora as they hardly penetrate into the pockets resulting from the disease.

Oral systemic administration of antibiotics has been shown to be a useful method of controlling the subgingival flora (Listgarten et al., 1978); however, while long-term therapy has the potential dangers associated with the development of resistant strains and super-imposed infections, discontinuation of therapy is often associated with the return of the potential pathogens to the pockets. In fact, due to side effects such as those of the digestive system, oral systematic administration has had only limited short term use, and variable success in treating periodontal disease (Genco, 1981).

Trying to overcome these difficulties, use of sustained release of drugs directly into the periodontal pocket has been tested, trying to achieve local drug concentration higher than that achieved by systematic administration.

Goodson et al. (1979 and 1985) proposed the use of a device that could be placed within the periodontal pocket and provide a sustained release of an antibacterial agent, e.g., for a period of up to 10 days. Particular such devices comprise a drug incorporated into a polymeric matrix, which is then shaped into a convenient form and implanted into the periodontal cavity. U.S. Pat. No. 4,175,326 describes the use of a drug-filled polymer hollow fiber. This delivery system is tied around a tooth and gently pressed below the margin of the gingiva such that it resides in the periodontal pocket, and is capable of delivering a dose of 2.5 micrograms tetracycline per day for a period of a week or more. Although these non-biodegradable devices are capable of dispensing an appropriate ingredient for a time span of a week or more, they are inappropriate for widespread use as they are difficult to apply and in certain cases must be dislodged in an operative procedure carried out by a dentist.

Degradable polymers and copolymers that have been substantially investigated as potential implant compositions include poly(lactic acid) (Kulkarni et al., 1966), poly(glygolic acid) (U.S. Pat. No. 2,676,945), and poly(lactic acid)poly(glycolic acid) copolymer (U.S. Pat. No. 3,397,033); and the properties and uses of such polymers and/or copolymers have been disclosed (FR 2,059,690 and FR 2,059,691; JP 72-43,220; U.S. Pat. No. 3,642,003). For example, the biodegradation of poly(lactic acid) and poly (glycolic acid) may require three to five months (FR 1,478,694; Darkik, 1971), and it may thus not be advisable to employ implants composed of such polymers where a more rapid biodegradation is desired.

Absorbable periodontal implants have been described by Noguchi et al. (1984), which used a hydroxypropylcellulose polymer. U.S. Pat. No. 4,569,837 discloses the use of water-soluble polymeric substances (such as methylcellulose, gelatin, etc.) as a polymeric matrix for a periodontal implant. Pharmaceutical compositions containing gelatin are disclosed in U.S. Pat. No. 2,961,374, U.S. Pat. No. 4,344,967 and U.S. Pat. No. 5,002,769, as well as in WO 2011/001425.

An alternative approach for delivering an active agent into the gingival pocket is by introducing said agent in a viscous gel form to the outer side of the inflamed gingival tissue; however, the drawback of this approach is the fast washout of the active agent by the saliva fluids or during eating. Hence, delivering of the active agent, in the form of an injectable fluid gel, directly inside the gingival pocket might be a better option.

A better alternative is by introducing said agent in a viscous gel form to the inner side of the inflamed gingival tissue. The benefit of this approach is almost a complete elimination of the washout of the active agent by the saliva fluids or during eating. However, the drawbacks of this approach are the difficulties in delivering an accurate amount of the gel into a pocket or reproducible amounts of the gel in each application; as well as the difficulty to entirely fill the pocket without leaving air pockets entrapped under the viscous gel.

Poloxamers have been widely used in the biomedical field due to their ability to undergo phase reverse thermal gelation. Their self-assembling process occurs through micellization, which is characterized by their critical micellization concentration and critical micellization temperature. These parameters, which depend on the specific poloxamer used, can be tailored to obtain materials with final properties suitable for a wide range of applications. Poloxamer gels are "generally regarded as safe" excipients, and have been widely investigated for delivery of active agents. One of the drawbacks associated to poloxamer gels for delivery applications is short residence times due to lack of adhesivness. Blending of poloxamers with mucoadhesive polymers that are capable of forming entanglements or non-covalent bonds with the mucus covering epithelial tissues is therefore one of the aproches to improve adhesiveness and residence time.

Hylauronic acid (also called hyaluronan or hyaluronate) is an anionic, nonsulfated glycosaminoglycan (GAG) widely distributed throughout connective tissues of vertebrates, being the most abundant glycosaminoglycan of higher molecular weight in the extracellular matrix of soft periodontal tissues. Hyaluronan has been found to be effective in treatment of inflammatory processes in medical areas such as orthopedics, dermatology and ophthalmology, and it has been further found to be anti-inflammatory and antibacterial in gingivitis and periodontitis therapy.

Treatment of plaque-induced gingivitis with hyaluronan in a gel formulation was reported by Jentsch et al. (2003), and the results were the basis for the commercially available product Gengigel®, containing high molecular weight hyaluronic acid (in the form of sodium hyaluronate).

Octenidine is an antimicrobial agent capable of inhibiting dental plaque (Bailey et al., 1984), which is used in the field of oral hygiene as a component of Octenidol® mouthwash.

Use of high molecular weight hyaluronan (molecular weight of $1\times10^6$ and $2.5\times10^6$ g/mol) with octenidine for healing and disinfecting a tooth extraction wound is disclosed in DE 202016102375 U1, wherein the preferred hyaluronan:octenidine ratio suggested is 500:1. According to this publication, a composition of these two ingredients may further comprise a polysaccharide and/or physiologically acceptable inorganic salt, capable of preventing or curing an inflammation of the alveolar bone that may occur as a postoperative complication of tooth extraction.

Atridox® is an antibiotic (doxycycline hyclate)-containing gel which is applied with a syringe into an infected gingival pocket and releases said antibiotic in a controlled-release manner. The product is marketed as a two syringe mixing system, wherein one syringe contains the ATRIGEL® delivery system (a polymeric delivery system consisting of a biodegradable poly (DL-lactide-co-glycolide) polymer formulation dissolved in a biocompatible solvent, N-methyl-2-pyrrolidone); and the other syringe contains the antibiotic agent. Upon contact with the crevicular fluid, the liquid product solidifies and then allows for controlled release of drug for a period of 7 days.

An acrylic strip made of polyethylmethacrylic impregnated with metronidazole, chlorhexidine acetate, or tetracycline is described in Addy et al. (1982). A similar strip made of ethyl cellulose, for drug release, is disclosed in U.S. Pat. No. 4,568,538. Ethylcellulose matrix polymer as periodontal implant was also described, e.g., in Friedman et al. (1982). Other non-biodegradable polymers tested for drug release for periodontal pockets include polyethylmethacrylate or biocompatible ethylene vinyl acetate (Goodson et al., 1983).

US 2015/0366975 discloses a thermosensitive injectable hydrogel, which has a gel formation temperature from 30° C. to 37° C., and comprises an hylauronic acid polymer and a copolymer of polyethylene oxide and polypropylene oxide, wherein the amounts of hylauronic acid polymer and the copolymer are about 0.005-0.3% (w/v) and about 12-20% (w/v), respectively. The hylauronic acid used has a molecular weight of $5000-20\times10^6$ Da, preferably $1.5\times10^6$-$2.5\times10^6$ Da. This publication further discloses a drug delivery system comprising said hydrogel and an active agent, e.g., an anticancer agrent, an antibiotic, or a wound healing agent.

EP 2520279 discloses a pharmaceutical composition in form of a thermoreversible gel, which comprises a topically active ingredient, e.g., a local disinfectant such as chlorhexidine; a thickening viscous matrix containing a poloxamer; and a muco-adhesive agent selected from hyaluronic acid or a derivative or salt thereof, that sticks the gel formulation to the oral mucosa or to the dental enamel.

U.S. Pat. No. 4,906,670 discloses a pharmaceutical composition for treatment of periodontal disease, comprising an active agent, e.g., a germicide such as chlorhexidine, benzalkonium chloride or cetylpyridinium chloride, dispersed in collagen.

U.S. Pat. No. 6,136,297 discloses a system for delivering an oral care substance, e.g., an antimicrobial agent such as octenidine, to a surface of an oral cavity.

SUMMARY OF INVENTION

In one aspect, the present invention provides a liquid composition comprising a non-biodegradable thermosensitive pharmaceutically acceptable polymer, more specifically polyalkylene oxide block copolymer; low molecular weight hyaluronic acid, more specifically hyaluronic acid having a molecular weight of up to about 50000 Da, or a salt thereof; and optionally a therapeutic agent, wherein said polymer is present in said composition in an amount of from about 21% to about 32% by weight; said hyaluronic acid or salt thereof is present in said composition in an amount of from about 0.01% to about 10% by weight; said composition has a viscosity of 100-2000, preferably 200-1000, centipoise (cP) at ambient temperature; and upon warming to body temperature, said composition solidifies into a viscous gel and then releases said hyaluronic acid and said therapeutic agent, when present, in a sustained release manner. Particular such compositions are those wherein the ratio between said polymer and said low molecular weight hyaluronic acid or salt thereof is in a range of from about 20:1 to about 50:1, from about 25:1 to about 40:1, or from about 30:1 to about 35:1.

In one particular such aspect, the liquid composition of the invention comprises no therapeutic agent, and upon warming to body temperature solidifies into a viscous gel and then releases said hyaluronic acid in a sustained release manner.

In another particular such aspect, the liquid composition of the invention comprises a therapeutic agent such as an antibacterial agent, and upon warming to body temperature solidifies into a viscous gel and then releases said hyaluronic acid and said therapeutic agent in a sustained release manner.

In another aspect, the present invention relates to a method for treatment of periodontal disease, gingival disease, peri-implantitis, or a disease or injury of the oral mucosa, in a subject in need thereof, said method comprising topically administering into a periodontal pocket, gingival pocket, or a pocket resulting from peri-implantitis, or applying on or into the oral mucosa, of said subject, a therapeutic agent-containing composition as defined above (e.g., such a composition comprising an antibacterial agent), to thereby release said therapeutic agent and said hyaluronic acid in said periodontal pocket, gingival pocket, or pocket resulting from peri-implantitis, or on or into said oral mucosa, respectively, in a sustained release maner.

In yet another aspect, the present invention relates to a therapeutic agent-containing composition as defined above (e.g., such a composition comprising an antibacterial agent) for use in the treatment of periodontal disease, gingival disease, peri-implantitis, or a disease or injury of the oral mucosa.

In a further aspect, the present invention relates to a kit for delivering a liquid composition into a periodontal pocket, gingival pocket, or a pocket resulting from peri-implantitis, or for applying said liquid composition on or into the oral mucosa, said kit comprising a therapeutic agent-containing composition as defined above (e.g., such a composition comprising an antibacterial agent); and a delivery mean, e.g., a syringe or an applicator, for topically administering said composition into said periodontal pocket, gingival pocket, or pocket resulting from peri-implantitis, or for applying said composition on or into said oral mucosa.

BRIEF DESCRIPTION OF DRAWINGS

FIGS. 2A-2B show pictures of Patient 2 in Table 2 before treatment with the Periodontal gel (t=0; 2A) and after three weeks of treatment with the gel (t=3 weeks; 2B).

DETAILED DESCRIPTION

Figure 1:
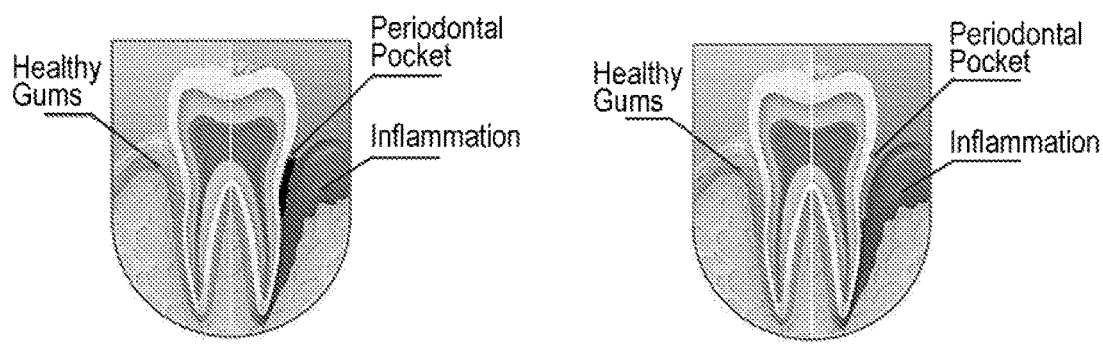
FIG. 1 shows a gingival pocket (right panel) and a gel-filled gingival pocket (left panel).
Figure 1:
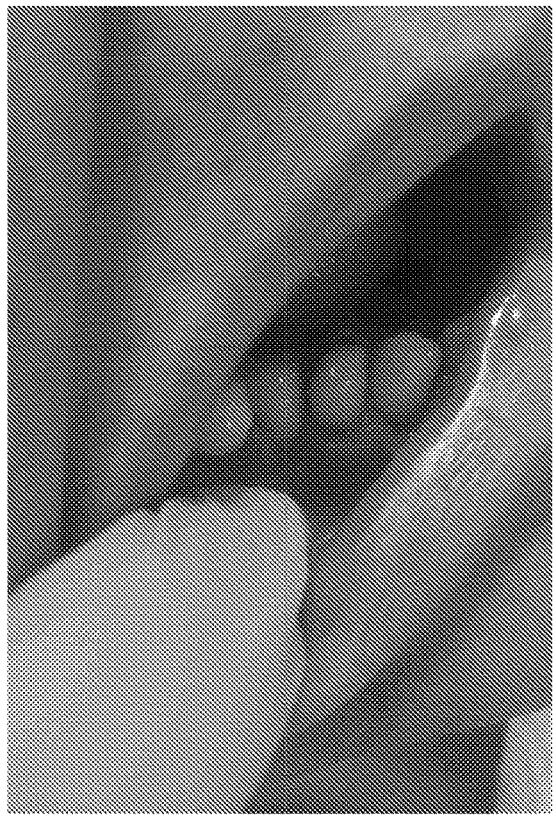
Figure 1:
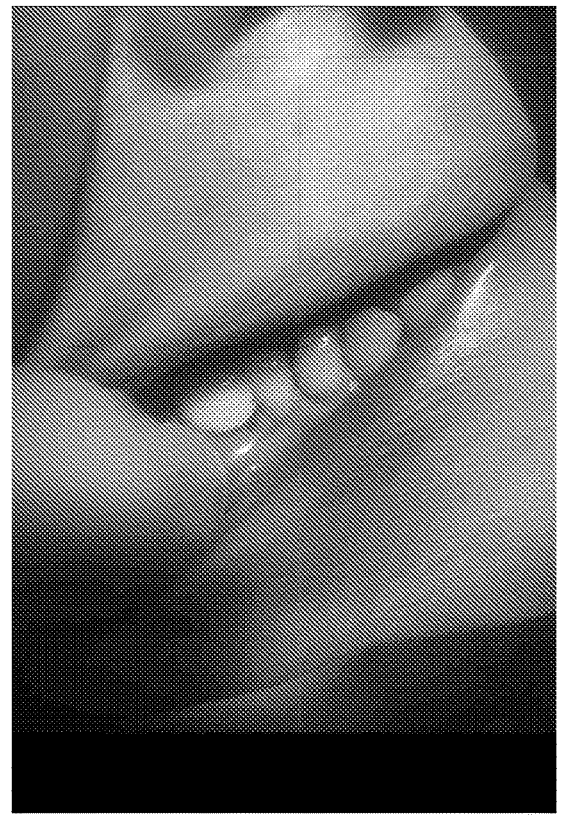

It has now been found, in accordance with the present invention, that a liquid composition comprising a non-biodegradable thermosensitive pharmaceutically acceptable polymer, more specifically a polyalkylene oxide block copolymer such as a poloxamer, and a glycosaminoglycan polymer, more specifically hyaluronic acid having a molecular weight of up to about 50000 Da, or a salt thereof, particularly wherein the ratio between said polymer and said hyaluronic acid or salt thereof is in a range of from about 20:1 to about 50:1, by weight, has low viscosity at ambient temperature; however, upon warming to body temperature solidifies into a viscous gel which serves as a vehicle for controlled release of a therapeutic agent, e.g., an antibacterial agent, comprised within, along with short hyaluronic acid chains. Such a therapeutic agent-containing liquid composition (referred to herein as "Periodontal gel"), when administered to a periodontal pocket, completely (or partially-at will) fills the pocket and then solidifies into a viscous gel that adheres and stays inside the inflammed pocket, and releases the therapeutic agent in a sustained release manner to thereby treat the periodontal disease (the short hyaluronic acid chains, which are capable of diffusing out of the gelatinous composition, further contribute to the healing process of the gingival tissue).

As surprisingly found, the polymer mixture composing the Priodontal gel undergoes a slow molecular rearrangement following the initial preparation, which results in high viscous matrix. Following this initial high viscosity stage, the composition viscosity decreases during the next several days after the preparation to reach the final desired fluid state. This finding was even more surprising as the phenomenon described above has not been observed when medium- or high-molecular weight (rather than low molecular weight) hyaluronic acid were used. The transition (decrease) in the composition viscosity, which occurs only when low molecular weight hyaluronic acid is used, allows the convenient injection of the composition at ambient temperature; enables to efficiently fill a periodontal pocket with the liquid composition injected (effective administration of a viscous gel into a periodontal pocket would be, physically, highly complicated, and even impossible in case said pocket consists of several pockets connected to each other); avoids the need to cool the composition, prior to injection, to a sub-ambient temperature; and thus prevents the injection of a cold composition that could have been much less convenient to the subject treated. With respect to particular such compositions exemplified herein, containing octenidine or a pharmaceutically acceptable salt thereof as the therapeutic agent, the fact that no cooling is required prior to injection is further advantageous as it prevents precipitation of the sparingly soluble octenidine without increasing the cosolvent (e.g., phenoxy ethanol) concentration in the composition, which would have resulted in a more irritating composition.

The terms "periodontal pocket", "periodontal crevice", "gingival pocket", "gingival crevice", and "dental pocket", used herein interchangeably, refer to an abnormal space between the cervical enamel of a tooth and the overlying unattached gingiva, resulting from a chronic inflammatory response associated with untreated gingivitis or periodontitis, which leads to desctruction and fracture of the bone and tissue supporting said tooth.

In one aspect, the present invention thus provides a liquid composition comprising a non-biodegradable thermosensitive pharmaceutically acceptable polymer, more specifically polyalkylene oxide block copolymer; hyaluronic acid having a molecular weight of up to about 50000 Da, or a salt thereof; and optionally a therapeutic agent, wherein said copolymer is present in said composition in an amount of from about 21% to about 32% by weight; said hyaluronic acid or salt thereof is present in said composition in an amount of from about 0.01% to about 10% by weight; said composition has a viscosity of 100-2000, preferably 200-1000, centipoise (cP; also referred to as millipascal seconds, mPa·sec) at ambient temperature; and upon warming to body temperature, said composition solidifies into a viscous gel and then releases said hyaluronic acid and said therapeutic agent, when present, in a sustained release manner.

The terms "sustained-release", "extended release" and "controlled release", used herein interchangeably, refers to the release of an active agent from a composition comprising it at predetermined intervals or gradually, in such a manner as to make the contained active agent available over an extended period of time, e.g., hours (e.g., up to 6, 12, 18, 24, 36, or 48 hours), days, or weeks. The release profile of the therapeutic agent from the composition of the present invention, after turning into a gel, depends on various parameters such as the particular non-biodegradable thermosensitive pharmaceutically acceptable polymer used, and its amount in the composition; and the ratio (by weight) between said polymer and the hyaluronan.

In certain embodiments, the non-biodegradable thermosensitive pharmaceutically acceptable polymer comprised within the composition of the invention is a poloxamer copolymer.

The term "poloxamer copolymer" as used herein denotes a polyethoxy/polypropoxy block copolymer, i.e., a nonionic triblock copolymer composed of a central hydrophobic chain of polyoxypropylene (poly(propylene oxide)) flanked by two hydrophilic chains of polyoxyethylene (poly(ethylene oxide)). Particualr examples of such poloxamers include, without being limited to, poloxamer 407, poloxamer 188, poloxamer 124, poloxamer 237, poloxamer 338, or a combination thereof.

The present invention does not require the use of polymers having a specific level of purity, and thus polymers of any grade of purity may be employed. Moreover, the composition disclosed herein may contain more than one thermosensitive pharmaceutically acceptable polymer. It is, however, preferable to employ polymers having a high degree of purity, and especially a defined (i.e., specifiable) composition, since the use of such polymers increases the degree with which the release of the therapeutic agent may be controlled.

In certain embodiments, the non-biodegradable thermosensitive pharmaceutically acceptable polymer is present in said composition in an amount of from about 22% to about 30% or from about 22% to about 28%, preferably from about 24% to about 28%, e.g., in an amount of about 24.0%, about 24.5%, about 25.0%, about 25.5%, about 26.0%, about 26.5%, about 27.0%, about 27.5%, or about 28%, by weight.

Hylauronic acid is an anionic, nonsulfated glycosaminoglycan (GAG) widely distributed throughout connective tissues of vertebrates, being the most abundant glycosaminoglycan of higher molecular weight in the extracellular matrix of soft periodontal tissues.

Hyaluronan has important hygroscopic, rheological and viscoelastic properties that fluctuate with changes in temperature, pH, ionic environment, and binding partners. However, these properties are also highly dependent on chain length. Hyaluronan can reach over $10^7$ Da in molecular mass, but also exists in multiple smaller forms, referred to as low molecular weight hyaluronan or oligomeric hyaluronan.

As disclosed in West and Kumar (1989), recombinant hyaluronan exerts varied bacteriostatic effects on all the bacterial strains tested, depending on its molecular weight and concentration, wherein high concentrations of medium molecular weight hyaluronan had the greatest bacteriostatic effect, particularly on the *Actinobacillus actinomycetemcomitans, Prevotella oris, Staphylococcus aureus,* and *Propionibacterium acnes* strains.

Hyaluronan has been found to be effective in treatment of inflammatory processes in medical areas such as orthopedics, dermatology and ophthalmology, and it has been further found to be anti-inflammatory and antibacterial in gingivitis and periodontitis therapy. Due to its tissue healing properties, it could be used as an adjunct to mechanical therapy in the treatment of periodontitis (Sukumar and Drizhal, 2007).

As previously shown, high molecular weight hyaluronan are immunosuppressive, antiangiogenic and anti-inflammatory, and were shown to protect against lymphocyte-mediated cytolysis (McBride and Bard, 1979), suppress septic responses to lipopolysaccharides, maintain immune tolerance, induce production of immunosuppressive macrophages, and reduce expression of inflammatory cytokines. Such hyaluronan was further found to have antiaging and anticancer effects; and are known to cause cell cycle arrest, mediated by transmembrane association between cluster of differentiation 44 (CD44) and the intracellular protein merlin (Morrison et al., 2001), and to protect against apoptosis by a mechanism mediated by nuclear factor kappa-B (NF-κB) (Jiang et al., 2005).

By contrast, short or low molecular weight hyaluronan are highly angiogenic, and immunostimulatory. Even the smallest fragment (the tetrasaccharide) has specific functions, with an ability to induce heat shock proteins and suppress apoptosis. The very smallest fragments apparently have the ability to ameliorate the intensity of the reactions induced by the small to intermediate-size fragments of hyaluronan. These small tetrameric to hexameric polysaccharides identify tissue injury. They also have the ability to inhibit the growth of tumor cells (Ghatak et al., 2002). It was shown that human umbilical cord hyaluronan that was hydrolyzed with hyaluronidase to molecular weight range of1350-4500Da 3-10 disaccharide units was angiogenetic, and when applied on skin of pig, can penetrate up to 800 μm and increase the number of blood vessels in the skin. In a study directed to the bacteriostatic effects of hyaluronic acid, it has been suggested that hyaloronan having molecular weight of 1300 kD may prove beneficial in minimizing bacterial contamination of surgical wounds when used in guided tissue regeneration surgery (Pirnazar et al., 1999).

Hyaluronan affects endothelial cell proliferation and monolayer integrity. In addition, oligosaccharides were found to stimulate angiogenesis in vivo and endothelial cells proliferation in vitro.

The hyaluronic acid or salt thereof comprised within the composition of the present invention is a low molecular weight hyaluronic acid, optionally hydrolyzed or partially hydrolyzed, more specifically hyaluronic acid having a molecular weight of up to about 50000 Da, or a salt thereof. In certain embodiments, said low molecular weight hyaluronic acid has a molecular weight of from about 3000 to about 50000 Da, from about 4000 to about 20000 Da, or from about 6000 to about 10000 Da. Hyaluronan having molecular weight of below 10000 Da is an important component of the extracellular matrix and has been used as a viscoelastic biomaterial for medical purposes, in cosmetics and as a drug delivery system.

In certain embodiments, the hyaluronic acid or salt thereof comprised with the composition of the present invention is present in an amount of from about 0.05%, 0.1%, 0.2%, 0.3%, 0.4% or 0.5% to about 10%, preferably from about 0.5% to about 5%, from about 0.5% to about 2%, or from about 0.5% to about 1.0%, more preferably from about 0.7% to about 0.9%, e.g., in an amount of 0.7%, 0.75%, 0.8%, 0.85%, or 0.9%, by weight.

Examples of hyaluronan salts include, without limiting, alkaline metal or alkaline earth metal salts of hyaluronan, e.g., sodium hyaluronate, potassium hyaluronate, and calcium hyaluronate.

The addition of hyaluronan to the thermosensitive polymer is intended to modify and improve the properties of the formulation which serves as carrier for the therapeutic agent. The interaction between poloxamer block polymers and hyaluronan have already been studied in the past. For example, Mayol el al. (2008) studied the influence of hyaluronic acid on the gelation properties of poloxamer blends with the aim of engineering thermosensitive and mucoadhesive polymeric platforms for drug delivery, and as found, the addition of hyaluronic acid did not hamper the self assembling process of poloxamers but reduced the gelation temperature by a few Celsius degrees. As further found, the presence of hyaluronic acid led to a strong increase of the poloxamer rheological properties, indicating possible interactions between the hyaluronic acid and micelles through secondary bonds, such as hydrogen bonds, which reinforce the gel structure.

In certain embodiments, the ratio between the non-biodegradable thermosensitive pharmaceutically acceptable polymer and the low molecular weight hyaluronan or salt thereof in the composition of the present invention is in a range of from about 20:1 to about 50:1, preferably from about 25:1 to about 40:1, more preferably from about 30:1 to about 35:1, e.g., about 30:1, about 30.5:1, about 31:1, about 31.5:1, about 32:1, about 32.5:1, about 33:1, about 33.5:1, about 34:1, about 34.5:1, or about 35:1 (polymer: hyaluronan or salt thereof, respectively), by weight.

In certain embodiments, the composition of the present invention comprises no therapeutic agent, and upon warming to body temperature solidifies into a viscous gel and then releases said hyaluronic acid in a sustained release manner.

In other embodiments, the composition disclosed herein comprises a therapeutic agent, e.g., an antiseptic agent, and is aimed at releasing said therapeutic agent, e.g., in a periodontal pocket, gingival pocket, or a pocket resulting from peri-implantitis; or on or into the oral mucosa, in a sustained release manner, i.e., in a predetermined rate aimed at maintaining a constant drug concentration for a specific period of time, e.g., hours or days, with minimum side effects.

The term "therapeutic agent" as used herein refers to any agent having a therapeutic effect that might be beneficial in treatment of periodontal disease, e.g., an antimicrobial agent; an antibacterial agent, also referred to herein as "antiseptic agent" or "disinfecting agent", more particularly a topical antiseptic agent; antifungal agent, also referred to herein as fungicide or fungistatic; an anti-inflammatory agent, e.g., a non-steroidal anti-inflammatory drug; an anti-pain agent; and a plant-derived therapeutic agent.

Examples of antifungal agents include, without being limited to, fluconazole, itraconazole, amphotericin B, voriconazole, nystatin, clotrimazole, econazole nitrate, miconazole, terbinafine, ketoconazole, enilconazole, boric acid, and miconazole The term "non-steroidal anti-inflammatory drug" (NSAID) as used herein refers to any non-steroidal anti-inflammatory drug/agent/analgesic/medicine, and relates to both cyclooxygenase (COX)-2 selective inhibitors such as celecoxib, rofecoxib, valdecoxib, parecoxib, etoricoxib and lumiracoxib, as well as to COX-2 non-selective inhibitors such as etodolac, aspirin, naproxen, ibuprofen, indomethacin, piroxicam and nabumetone.

Examples of anti-pain agents include, without being limited to, a local anesthetic, lidocaine, benzocaine, dibucaine, tetracaine, and proparacaine.

Topical antiseptics in general are less likely to induce resistance compared with antibiotics, owing to their unspecific mode of action and the high concentrations in which they can be used. In certain embodiments, the antibacterial agent comprised within the oral delivery composition of the present invention is a topical antibacterial agent such as a quaternary ammonium compound (QAC) or a pharmaceutically acceptable salt thereof, e.g., benzalkonium chloride, or cetylpyridinium chloride; a guanidine compound or a pharmaceutically acceptable salt thereof, e.g., chlorhexidine, alexidine, or polyhexamethylene biguanide (PHMB); hexetidine, triclosan; liniment (Glossary of common dental product ingredients. Version one: May 2011. British dental health foundation); stannous fluoride; eucalyptol; menthol; methyl slisylate; thymol; peppermint oil; amyloglucosidase; or glucose oxidase (Silje Storehagen, Nanna Ose og Shilpi Midha. Dentifrices and mouthwashes ingredients and their use. Thesis for degree Candidata Odontologiae (DDS). Faculty of dentistry, University of Oslo, 2003).

In other embodiments, the topical antiseptic agent comprised within the oral delivery composition of the present invention is the bispyridinamine octenidine (1,1',4,4'-tetrahydro-N,N'-dioctyl-1,1'-decametylenedi-(4-pyridylide-neamine)), an antimicrobial agent capable of inhibiting dental plaque (Bailey et al., 1984), or a pharmaceutically acceptable salt thereof such as octenidine dihydrochloride (CAS-number 70775-75-6) that is exemplified herein. Octenidine dihydrochloride is a cationic, surface active antimicrobial compound, which differs from QACs such as benzalkonium chloride, and guanidines such as chlorhexidine, by the lack of an amide- and ester structure in its molecule, which results in lower toxicity due to possible metabolites. Octenidine can be sterilized by steam up to 130° C. in aqueous solutions and stored at room temperature, making it suitable for long storage. The stability of octenidine makes it a useful robust molecule that is insensitive to interactions with functional groups that might be present in the composition (e.g., during preparation and/or storage of the composition). Moreover, octenidine is stable and maintains its antimicrobial activity at an extremely broad pH range (1.6-12.2), which is particularly important in wound healing during which the wound pH changes. The octenidine mode of action involves destabilization of the microorganism membrane, and this ensures that microorganisms exposed to said agent cannot develop drug resistance in a straightforward way, as the entire cellular structure, rather than a specific molecular target, is affected. Since octenidine is a hydrophobic compound, it requires an organic solvent such as ethanol or phenoxyethanol in order to be effectively administered. However, such organic solvents may cause substantial irritation, particularly when applied to inflamed tissue, and the drug should thus be introduced in a suitable manner, e.g., in a controlled release manner precisely at the site of microbial contamination (e.g., the periodontal pocket).

In particular embodiments, the topical antiseptic agent comprised within the oral delivery composition of the invention is octenidine, or a pharmaceutically acceptable salt thereof such as octenidine dihydrochloride. Examples of other pharmaceutically acceptable salts of octenidine include, without limiting, the dimesylate salt, the diesylate salt, the ditosylate salt, the disulfate salt, the disulfonate salt, the diphosphate salt, the dicarboxylate salt, the dimaleate salt, the difumarate salt, the ditartrate salt, the dicitrate salt, the dibenzoate salt, the diacetate salt, the dihydrobromide salt, and the digluconate salt.

In certain embodiments, the antibacterial agent comprised within the composition of the present invention is present at a concentration of from about 0.01% to about 5%, preferably from about 0.05% to about 4%, from about 0.1% to about 3%, or from about 0.3% to about 1%, more preferably from about 0.5% to about 0.7%, e.g., at a concentration of about 0.5%, about 0.525%, about 0.55%, about 0.575%, about 0.6%, about 0.625%, about 0.65%, about 0.675%, or about 0.7%, by weight.

Use of high molecular weight hyaluronan (molecular weight of $1 \times 10^6$ and $2.5 \times 10^6$ g/mol) with octenidine is disclosed in DE 202016102375 U1.

In certain embodiments, the present invention provides a liquid composition as defined in any one of the embodiments above, wherein the non-biodegradable thermosensitive pharmaceutically acceptable polymer is a poloxamer; said hyaluronic acid has a molecular weight of from about 3000 to about 50000 Da, preferably from about 4000 to about 20000 Da, more preferably from about 6000 to about 10000 Da; and said therapeutic agent is an antibacterial agent such as octenidine or a pharmaceutically acceptable salt thereof, e.g., octenidine dihydrochloride. In particular such embodiments, said poloxamer is poloxamer 407, poloxamer 188, poloxamer 124, poloxamer 237, poloxamer 338, or a combination thereof; and said hyaluronic acid has a molecular weight of from about 4000 to about 20000 Da, preferably from about 6000 to about 10000 Da. More particular such embodiments are those wherein (i) said polymer is present in said composition in an amount of from about 22% to about 30%, or from about 24% to about 28%, by weight; (ii) said hyaluronic acid or salt thereof is present in said composition in an amount of from about 0.05% to about 1.0%, or from about 0.5% to about 1.0%, or from about 0.7% to about 0.9%, by weight; (iii) the ratio between said polymer and said hyaluronic acid or salt thereof is in a range of from about 25:1 to about 40:1, or from about 30:1 to about 35:1 (polymer:hyaluronan or salt thereof, respectively), by weight; and (iv) said antibacterial agent is present at a concentration of from about 0.4% to about 0.9%, or from about 0.5% to about 0.7%, by weight.

The liquid compositions of the present invention may be prepared according to any procedure and utilizing any technique available, e.g., according to the process described in detail in the Examples section hereinafter.

The liquid composition as defined in any one of the embodiments above may further comprise one or more additional therapeutical agents, e.g., one or more anti-inflammatory agents in addition to the hyaluronan that has an anti-inflammatory activity.

In another aspect, the present invention relates to a method for treatment of periodontal disease, gingival disease, peri-implantitis, or a disease or injury of the oral mucosa, in a subject in need thereof, said method comprising topically administering into a periodontal pocket, gingival pocket, or a pocket resulting from peri-implantitis, or applying on or into the oral mucosa, of said subject, a Periodontal gel, i.e., a therapeutic agent-containing liquid composition as defined in any one of the embodiments above (e.g., such a composition comprising an antibacterial agent), to thereby release said therapeutic agent and said hyaluronic acid or salt thereof in said periodontal pocket, gingival pocket, or pocket resulting from peri-implantitis, or on or into said oral mucosa, respectively, in a sustained release manner.

The term "subject" as used herein refers to any mammal, e.g., a human, non-human primate, horse, ferret, dog, cat, cow, and goat. In a preferred embodiment, the term "subject" denotes a human, i.e., an individual.

In certain embodiments, the method of the present invention comprises topically administering a liquid composition as defined in any one of the embodiments above, wherein said non-biodegradable thermosensitive pharmaceutically acceptable polymer is a poloxamer; said hyaluronic acid has a molecular weight of from about 3000 to about 50000 Da, from about 4000 to about 20000 Da, or from about 6000 to about 10000 Da; and said therapeutic agent is an antibacterial agent such as octenidine or a pharmaceutically acceptable salt thereof, e.g., octenidine dihydrochloride. In particular such embodiments, said poloxamer is poloxamer 407, poloxamer 188, poloxamer 124, poloxamer 237, poloxamer 338, or a combination thereof; and said hyaluronic acid has a molecular weight of from about 4000 to about 20000 Da, or from about 6000 to about 10000 Da. More particular such embodiments are those wherein (i) said polymer is present in said composition in an amount of from about 22% to about 30%, or from about 24% to about 28%, by weight; (ii) said hyaluronic acid or salt thereof is present in said composition in an amount of from about 0.05% to about 1.0%, or from about 0.5% to about 1.0%, or from about 0.7% to about 0.9%, by weight; (iii) the ratio between said polymer and said hyaluronic acid or salt thereof is in a range of about 25:1 to about 40:1, or from about 30:1 to about 35:1 (polymer:hyaluronan or salt thereof, respectively), by weight; and (iv) said antibacterial agent is present at a concentration of from about 0.4% to about 0.9%, or from about 0.5% to about 0.7%, by weight.

In yet another aspect, the present invention relates to a therapeutic agent-containing composition as defined above (e.g., such a composition comprising an antibacterial agent) for use in the treatment of periodontal disease, gingival disease, peri-implantitis, or a disease or injury of the oral mucosa.

The Periodontal gel (cold solution) disclosed herein may be packed in a suitable sealed syringe equipped with a suitable blunt needle, wherein the amount of said liquid composition in the syringe may be sufficient for treating varying number of gingival pockets (e.g., about 0.7 ml to about 1.2 ml). Such a syringe may be equipped with 25G needle or tip for optimal injection; however, smaller or larger gauge can be used as well. The syringe is best operated at either ambient or below ambient temperature where the viscosity is low enough to allow precise and controlled delivery without exerting excessive pressure. At this temperature, a dentist can deliver the right amount of liquid composition directly to the bottom of the gingival pocket, where it will turn into gel that will adhere and stay inside the pocket. Upon gelation, the highly viscous structure prevents bacteria from reinfesting the pocket, and controls the release of the therapeutic agent, e.g., octenidine, to the inflamed gingival inner pocket wall, in a sustained manner, i.e., during hours and up to several days.

The initial release of the therapreutic agent from the Periodontal gel is extensive enough to build, in a short time, a high concentration of the therapeutic agent inside the periodontal pocket, and the gel is is then lowly dissolved within the gingival crevicular fluid allowing continuous and slow release of the therapeutic agent, along with the release of short chain hyaluronan that aids in healing the inflamed gingival pocket tissue.

In a further aspect, the present invention thus relates to a kit for delivering a liquid composition into a periodontal pocket, gingival pocket, or a pocket resulting from peri-implantitis, or for applying said liquid composition on or into the oral mucosa, said kit comprising a therapeutic agent-containing liquid composition as defined in any one of the embodiments above (e.g., such a composition comprising an antibacterial agent); and a delivery mean for topically administering said composition into said periodontal pocket, gingival pocket, or pocket resulting from peri-implantitis, or for applying said composition on or into said oral mucosa.

In certain embodiments, the kit disclosed herein comprises a liquid composition as defined in any one of the embodiments above, wherein said non-biodegradable thermosensitive pharmaceutically acceptable polymer is a poloxamer; said hyaluronic acid has a molecular weight of from about 3000 to about 50000 Da, from about 4000 to about 20000 Da, or from about 6000 to about 10000 Da; and said therapeutic agent is an antibacterial agent such as octenidine or a pharmaceutically acceptable salt thereof, e.g., octenidine dihydrochloride. In particular such embodiments, said poloxamer is poloxamer 407, poloxamer 188, poloxamer 124, poloxamer 237, poloxamer 338, or a combination thereof; and said hyaluronic acid has a molecular weight of from about 4000 to about 20000 Da, or from about 6000 to about 10000 Da. More particular such embodiments are those wherein (i) said polymer is present in said composition in an amount of from about 22% to about 30%, or from about 24% to about 28%, by weight; (ii) said hyaluronic acid or salt thereof is present in said composition in an amount of from about 0.05% to about 1.0%, or from about 0.5% to about 1.0%, or from about 0.7% to about 0.9%, by weight; (iii) the ratio between said polymer and said low molecular weight hyaluronic acid or salt thereof is in a range of about 25:1 to about 40:1, or from about 30:1 to about 35:1 (polymer:hyaluronan or salt thereof, respectively), by weight; and (iv) said antibacterial agent is present at a concentration of from about 0.4% to about 0.9%, or from about 0.5% to about 0.7%, by weight.

The delivery mean included in the kit disclosed herein may be any mean capable of administering or applying a predetermined amount of a liquid composition as defined herein to a periodontal pocket or gingival pocket, e.g., an applicator or a syringe optionally with a blunt needle. In particular embodiments, the kit of the invention comprises a syringe with a blunt needle, capable of administering one or more doses of a liquid composition as defined above to a periodontal pocket or gingival pocket.

Unless otherwise indicated, all numbers expressing quantities of ingredients and so forth used in the present description and claims are to be understood as being modified in all instances by the term "about". Accordingly, unless indicated to the contrary, the numerical parameters set forth in this description and attached claims are approximations that may vary by up to plus or minus 10% depending upon the desired properties sought to be obtained by the present invention.

The invention will now be illustrated by the following non limiting Examples.

EXAMPLES

Study 1. Preparation of a <10kDa Hyaluronic Acid-Based Periodontal Gel

A poloxamer powder such as Synperonic™ PE/F127 (Croda Crop Care) is added in small portions into cold pure water at a temperature below 10° C. and dissolved under vigorous mixing for at least 4 hours. The clear solution is left refrigerated overnight to allow full swelling of the polymer chains. Into the cold clear solution, the short chain oligomeric hyaluronic acid (Bloomage Freda Biopharm Co., Ltd., Oligo Hyaluronic Acid [HA-Oligo], <10 kDa, http://www.bloomagefreda.com/proen/id/16.html) in powder form is added and mixed until full dissolution. The polymer mixture solution thus obtained is kept cold to avoid temperature rise and hardening and gelation of the thermosensitive solution. Octenidine active powder is dissolved in phenoxyethanol at 40-45° C. Part of the warm octenidine in phenoxyethanol is cooled to ambient temperature and mixed into the cold polymer mixture solution. In case the solution starts to harden during mixing, the system should be ice cooled again to reduce viscosity, to enable efficient mixing to reach a homogenuous mixture. Once the mixture becomes homogenuous it is left to warm up to ambient (room) temperature. Once the preparation reaches room temperatre it turns into a viscous thick gel having a viscosity that is much higher than the desired one that would allow the injection of the preparation into a periodontal pocket. As the last step, in order to reach the desired temporary low viscosity, the preparation is left at room temperature for several days, during which it undergoes aging process where the viscosity falls down dramatically and surprisingly until the preparation becomes a fluid with a low viscosity in the range of 100-2000 cP, which can be injected, e.g., via 25G needle, and fill up periodontal pockets with no air bubbles trapped in the pockets. This unique liquid preparation, upon injection into a periodontal pocket, penetrates into the deepest cavity of the pocket, and then turns into hard viscous thick gel that adheres firmly where it was placed, and can hardly be secreted from the pocket.

In general, the thermoreversible change in thermosensitive compositions from liquid to gelatinous state following temperature increase is almost instantaneous. Yet, as surprisingly found, the mixture of components used for the preparartion of the Priodontal gel undergoes a slow molecular rearrangement, following which the composition viscosity decreases several days after preparation, such that it can be conveniently injected at ambient temperature. This finding was even more surprising as the phenomenon described above has not been observed when medium or high molecular weight (rather than low molecular weight) hyaluronic acid were used. For example, using the same weight percent of hyaluronic acid having molecular weight of about $1.5 \times 10^6$ Da resulted with a high viscosity solution which was maintained more or less stable during several days. The favorable transition in the viscosity of the composition when low molecular weight hyaluronic acid is used allows the convenient injection of the composition at ambient temperature; avoids the need to cool the composition, prior to injection, to a sub-ambient temperature (necessitates a cooling device and time); and thus prevents the injection of a cold composition that could have been much less convenient to the individual treated. The fact that no cooling is required prior to injection is further advantageous as it prevents precipitation of the sparingly soluble octenidine without increasing the cosolvent (e.g., phenoxy ethanol) concentration in the composition, which would have resulted in a more irritating composition.

The slow reduction in viscosity observed when using low molecular weight hyaluronan chains, but not in case higher molecular weight hyaluronan chains are used, can be explained by a slow diffusion and re-arrangement of the low molecular weight hyaluronan chains in between the polymer structure (poloxamer gel). Such diffusion is highly restricted once the hyaluronan chain length and molecular weight increase. The diffusion within the poloxamer gel molecular assembly with the following reduction of the preparation viscosity (from gel state into liquid state) suggests that low molecular weight hyaluroinic acid chains are further capable of diffusing out of the gelatinous composition (once inside the periodontal pocket) into the gingival pocket. This way, the controlled release of the antiseptic octenidine occurs in parallel to a slow release of the hyaluronan molecules into the surrounding gingival tissue, which further aids with the healing process.

The preparation may be packed in a suitable sealed syringe equipped with a suitable blunt needle. The syringe is filled with a suitable amount of liquid (e.g., about 0.7 ml to about 1.2 ml) sufficient to treat varying number of pockets. The syringe may be equipped with 25G needle or tip for optimal injection; however, smaller gauge can be used as well. The syringe is best operated at either ambient or below ambient temperature where the viscosity is low enough to allow precise and controlled delivery without exerting excessive pressure. At this temperature the dentist can deliver the right amount of composition directly to the bottom of the gingival pocket, where upon warming towards body temperature, it will turn into gel that will adhere and stay inside the pocket. Upon gelation, the highly viscous structure further acts as a barrier controlling the release of the octenidine to the inflamed gingival inner pocket wall, in a sustained manner, i.e., during hours and up to several days.

Table 1 shows the effect of hyaluronan molecular weight on the viscosity at room temperature and syringeability of the composition prepared.

In order to examine the efficacy of the Periodontal gel, three patients with periodontal pockets of various depths were treated. Pocket depth and level of gum inflammation were recorded, clearly showing the initial beneficial effect in decreasing the level of gum inflammation (Table 2). FIG. 2 shows pictures of Patient 2 in Table 2 before treatment with the Periodontal gel (at t=0; FIG. 2A) and after three weeks of treatment with the gel (at t=3 weeks; FIG. 2B).

Study 2. Preparation of a ~48 kDa Hyaluronic Acid-Based Periodontal Gel

In order to check the effect of the molecular weight of the hyaluronic acid, or the concentration thereof, on the physical properties of the composition, various compositions were prepared with different weight concentrations of hyaluronic acid having a molecular weight of either <10 kDa (as exemplified in Study 1), or ~48 kDa using a particular batch of hyaluronic acid having a molecular weight of ~48 kDa (Bloomage Freda Biopharm Co., Ltd., Hyaluronic Acid [HA-TLM], http://www.bioomagefreda.com/proen/id/16.html). The compositions were prepared following the exact procedure described in Study 1, and were examined for their physical appearance, syringeability at room temperature, and viscosity at 20° C. and 37° C. Table 3 summarizes the information about the compositions prepared and their properties.

As shown in Table 3, at room temperature, each one of the compositions was in the form of a liquid-like transparent flowing gel having a maximal viscosity of 585 cPs, except for composition number 3 (8.0% by weight hyaluronic acid having a molecular weigth of <10 kDa) which had viscosity of 1700 cPs, and all the compositions passed the syringeability test. Upon warming to body temperature, all the compositions were solidified into a strong viscous gel.

TABLE 1

The effect of hyaluronic acid molecular weight (MW) on the viscosity at room temperature (RT) and syringeability of the composition

| Hyaluronic acid MW | Physical state (RT, a week after completion of production) | Syringeability 25 G (RT) | Syringeability 25 G (6° C.) | Viscosity 20° C. |
|---|---|---|---|---|
| MW < 10 kDa | Liquid-like flowing gel | Pass | Pass | 566-585 cPs (sp. 03)[a,b] |
| 200 kDa < MW < 400 kDa | Solid gel (smooth) | Fail | Fail | 8600-9166 cPS (sp. 06)[a,c] |
| 1.0 MDa < MW < 1.8 MDa | Solid gel (with trapped bubbles) | Fail | Fail | <50000 cPS |

\* Viscosity was measured using Brookfield viscometer model RVDV –I+, USA.

[a]sp. - spindle number;
[b]measured at 20° C.;
[c]measured at 17° C.

TABLE 2

The efficacy of the Periodontal gel in reducing the level of gum inflammation

| Patient | Age | Sex | | Tooth | Placement | Pocket Depth (mm) | Mobility | Level of gum inflammation (0-4; 4 = worst) |
|---|---|---|---|---|---|---|---|---|
| 1 | 71 | F | t = 0 | 13 | M | 6 | 0 | 4 |
| | | | after 1 month | | M | 6 | 0 | 2 |
| | | | after 2 months | | M | 6 | 0 | 1 |
| | | | after 3 months | | M | 5 | 0 | 0 |
| 2 | 47 | F | t = 0 | 47 | M | 7 | 1 | 4 |
| | | | after 1 week | | M | 7 | 1 | 1 |
| | | | after 3 weeks | | M | 6 | 1 | 0 |
| 3 | 35 | F | t = 0 | all | all | 4 to 7 | 0 | 3 |
| | | | after 1 week | | all | 4 to 7 | 0 | 2 |

TABLE 3

Various compositions prepared and their physical properties

| Sample | Hyaluronic acid | Hyaluronic acid concentration (by weight) | Viscosity* at 20° C. |
|---|---|---|---|
| 1 | <10 (~8) kDa | 0.8% | 566-585 cPs (sp. 03, 100 rpm) |
| 2 | <10 (~8) kDa | 3.0% | 570-580 cPs (sp. 03, 100 rpm) |
| 3 | <10 (~8) kDa | 8.0% | 1700 cPs (sp. 05, 20 rpm) |
| 4 | 48 kDa | 0.1% | 430-440 cPs (sp. 03, 100 rpm) |
| 5 | 48 kDa | 0.5% | 570-580 cPs (sp. 03, 100 rpm) |

*Measured using Brookfield viscometer model RVDV –I+, USA; sp. - spindle number.

REFERENCES

Addy, M.; Rawle, L.; Handley, R.; Newman, H. N.; Coventry, J. F. *J. Periodontol.* 1982, 53(11), 693-699

Bailey, D. M.; DeGrazia, C. G.; Hoff, S. J.; Schulenberg, P. L.; O'Connor, J. R.; Paris, D. A.; Slee, A. M. *J Med Chem.* 1984, 27(11), 1457-1464

Darkik, *Am. J. Surg.* 1971, 121, 656

Friedman, M.; Golomb, G. *J. Periodon. Res.* 1982, 17, 323-328

Ghatak, S; Misra, S; Toole, B. P. *J Biol Chem.* 2002, 277, 38013-20

Genco, R. J. *J. Periodontol.* 1981, 52(9), 545-558

Goodson, J. M.; Haffajee, A.; Socransky, S. S. *J. Clin. Periodont.* 1979, 6(2), 83-92

Goodson, J. M.; Jolborow, D.; Dunn, R. L., Hogan, P.; Dunham, S. J. Periodontol. 1983, 54(10), 575-579

Goodson, J. M.; Hogan, P. E.; Dunham, S. L. *J Periodontol.* 1985, 56(11 Suppl), 81-87

Jentsch, H.; Pomowski, R.; Kundt, G.; Gocke, R. *J Clin Periodontal.* 2003, 30(2), 159-164

Jiang, D.; Liang, J.; Fan, J.; Yu, S.; Chen, S.; Luo, Y.; Prestwich, G. D.; Mascarenhas, M. M.; Garg, H. G.; Quinn, D. A.; Homer, R. J.; Goldstein, D. R.; Bucala, R.; Lee, P. J.; Medzhitov, R.; Noble, P. W. *Nat Med.* 2005, 11(11), 1173-1179

Kulkarni, R. K.; Pani, K. C.; Neuman, C.; Leonard, F. *Arch. Surg.* 1966, 93(5), 839

Loe, H.; Schiott, C. R. *J. Periodont. Res.* 1970, 5(2), 79-83

Listgarten, M. A.; Lindhe, J.; Hellden, L. *J Clin Periodontol.* 1978, 5(4), 246-271

Mayol, L.; Quaglia, F.; Borzacchiello, A.; Ambrosio, L.; La Rotonda, M. I.; *Eur J Pharm Biopharm.,* 2008, 70(1), 199-206

McBride, W. H.; Bard, J. B. *J Exp Med.* 1979, 149(2), 507-515

Morrison, H.; Sherman, L. S.; Legg, J.; Banine, F.; Isacke, C.; Haipek, C. A.; Gutmann, D. H.; Ponta, H.; Herrlich, P. *Genes Dev.* 2001, 15(8), 968-980

Noguchi,T.; Izumizawa, K.; Fukada, M.; Kitamura, S.; Suzuki, Y.; Ikura, H. *Bull. Tokyo Med. Dent. Univ.* 1984, 31, 145

Pirnazar, P.; Wolinsky, L.; Nachmani, S.; Haake, S.; Pilloni, A.; Bernard, G. W. *J Periodontol* 1999, 70(4), 370-374

Sukumar, S.; Drizhal, I. *Acta Medica* (Hradec Kralove), 2007, 50(4), 225-228

West, D. C.; Kumar, S. *Ciba Found Symp.* 1989, 143, 187-201

What is claimed is:

1. A liquid composition comprising a non-biodegradable thermosensitive pharmaceutically acceptable poloxamer copolymer, hyaluronic acid or a salt thereof, and optionally a therapeutic agent,
wherein said copolymer is present in said composition in an amount of from 21% to 32% by weight; said hyaluronic acid has a molecular weight of up to 50000 Da, and said hyaluronic acid or salt thereof is present in said composition in an amount of from 0.01% to 10% by weight; said composition is free of hyaluronic acid with a molecular weight greater than 50000 Da; and said composition has a viscosity of 100-2000 centipoise (cP) at 20° C., when measured with Brookfield viscosimeter RVDV –I+, at either spindle number 03 and 100 rpm, or spindle number 05 and 20 rpm; and upon warming to body temperature, said composition solidifies into a viscous gel and then releases said hyaluronic acid and said therapeutic agent, when present, in a sustained release manner.

2. The composition of claim 1, wherein said poloxamer copolymer is poloxamer 407, poloxamer 188, poloxamer 124, poloxamer 237, poloxamer 338, or a combination thereof.

3. The composition of claim 2, wherein said poloxamer copolymer is poloxamer 407.

4. The composition of claim 1, wherein said poloxamer copolymer is present in said composition in an amount of from 22% to 30% by weight.

5. The composition of claim 1, wherein said hyaluronic acid has a molecular weight of from 3000 to 50000 Da.

6. The composition of claim 1, wherein said hyaluronic acid or salt thereof is present in said composition in an amount of from 0.05% to 10% by weight.

7. The composition of claim 1, wherein the ratio between said poloxamer copolymer and said hyaluronic acid or salt thereof is in a range of from 20:1 to 50:1 by weight.

8. The composition of claim 1, wherein said therapeutic agent is present and selected from an antimicrobial agent, antibacterial agent, antifungal agent, anti-inflammatory agent, or anti-pain agent.

9. The composition of claim 8, wherein said therapeutic agent is an antibacterial agent.

10. The composition of claim 9, wherein said antibacterial agent is a topical antibacterial agent selected from a quaternary ammonium compound, a guanidine compound, hexetidine, octenidine, or a pharmaceutically acceptable salt thereof.

11. The composition of claim 10, wherein said quaternary ammonium compound is benzalkonium chloride, or cetylpyridinium chloride; and said guanidine compound is alexidine, or polyhexamethylene biguanide.

12. The composition of claim 10, wherein said antibacterial agent is octenidine, or a pharmaceutically acceptable salt thereof.

13. The composition of claim 9, wherein said antibacterial agent is present at a concentration of from 0.01% to 5% by weight.

14. The composition of claim 1, wherein said hyaluronic acid has a molecular weight of from 3000 to 50000 Da; and said therapeutic agent is an antibacterial agent.

15. The composition of claim 14, wherein said poloxamer copolymer is poloxamer 407, poloxamer 188, poloxamer 124, poloxamer 237, poloxamer 338, or a combination thereof; and said hyaluronic acid has a molecular weight of from 4000 to 20000 Da.

16. The composition of claim 15, wherein said poloxamer copolymer is poloxamer 407.

17. The composition of claim 15, wherein (i) said poloxamer copolymer is present in said composition in an amount of from 22% to 30% by weight; and (ii) said hyaluronic acid or salt thereof is present in said composition in an amount of from 0.05% to 1.0% by weight; and (iii) the ratio between said poloxamer copolymer and said hyaluronic acid or salt thereof is in a range of from 25:1 to 40:1 by weight; and (iv) said antibacterial agent is present at a concentration of from 0.4% to 0.9% by weight.

18. The composition of claim 16, wherein (i) said poloxamer copolymer is present in said composition in an amount of from 22% to 30% by weight; and (ii) said hyaluronic acid or salt thereof is present in said composition in an amount of from 0.05% to 1.0% by weight; and (iii) the ratio between said poloxamer copolymer and said hyaluronic acid or salt thereof is in a range of from 25:1 to 40:1 by weight; and (iv) said antibacterial agent is present at a concentration of from 0.4% to 0.9% by weight.

19. The composition of claim 14, wherein said antibacterial agent is octenidine or a pharmaceutically acceptable salt thereof.

20. A method for treatment of periodontal disease, gingival disease, peri-implantitis, or a disease or injury of the oral mucosa, in an individual in need thereof, said method comprising topically administering into a periodontal pocket, gingival pocket, or a pocket resulting from peri-implantitis, or applying on or into the oral mucosa, of said individual, a composition according to claim 1 wherein said therapeutic agent is present, to thereby release said therapeutic agent in said periodontal pocket, gingival pocket, or pocket resulting from peri-implantitis, or on or into said oral mucosa, respectively, in a sustained release manner.

21. The method of claim 20, wherein said hyaluronic acid has a molecular weight of from 3000 to 50000 Da; and said therapeutic agent is an antibacterial agent.

22. The method of claim 21, wherein said poloxamer copolymer is poloxamer 407, poloxamer 188, poloxamer 124, poloxamer 237, poloxamer 338, or a combination thereof; and said hyaluronic acid has a molecular weight of from 4000 to 20000 Da.

23. The method of claim 22, wherein (i) said poloxamer copolymer is present in said composition in an amount of from 22% to 30% by weight; and (ii) said hyaluronic acid or salt thereof is present in said composition in an amount of from 0.05% to 1.0% by weight; and (iii) the ratio between said poloxamer copolymer and said hyaluronic acid or salt thereof is in a range of 25:1 to 40:1 by weight; and (iv) said antibacterial agent is present at a concentration of from 0.4% to 0.9% by weight.

24. The method of claim 21, wherein said antibacterial agent is octenidine or a pharmaceutically acceptable salt thereof.

25. A kit for delivering a liquid composition into a periodontal pocket, gingival pocket, or a pocket resulting from peri-implantitis, or for applying said liquid composition on or into the oral mucosa, said kit comprising a composition according to claim 1; and a delivery means for topically administering said composition into said periodontal pocket, gingival pocket, or pocket resulting from peri-implantitis, or for applying said composition on or into said oral mucosa.

26. The kit of claim 25, wherein said delivery mean is a syringe, or an applicator.

* * * * *